United States Patent [19]
Myers

[11] Patent Number: 5,617,897
[45] Date of Patent: Apr. 8, 1997

[54] NONRETURN VALVE FOR MEDICAL FLUID TECHNOLOGIES

[75] Inventor: Jan W. M. Myers, Venlo, Netherlands

[73] Assignee: Schawk, Inc

[21] Appl. No.: 197,999

[22] Filed: Feb. 16, 1994

[30] Foreign Application Priority Data

Feb. 18, 1993 [DE] Germany .................. 43 04 949.4

[51] Int. Cl.⁶ .................................................. F16K 15/14
[52] U.S. Cl. ................................... 137/859; 604/247
[58] Field of Search ................................ 137/859; 604/247

[56] References Cited

U.S. PATENT DOCUMENTS

| | | | |
|---|---|---|---|
| 2,758,609 | 8/1956 | Dickert et al. | 137/859 |
| 3,084,707 | 4/1963 | Frye | 137/859 X |
| 3,270,771 | 9/1966 | Morgan et al. | 137/859 |
| 3,599,657 | 8/1971 | Maldaus | 137/859 X |
| 4,089,349 | 5/1978 | Schenk | 137/859 |
| 4,593,720 | 6/1986 | Bergandy | 137/859 |
| 4,712,583 | 12/1987 | Pelmulder et al. | 137/859 X |
| 4,768,547 | 9/1988 | Danby et al. | 137/859 X |
| 5,025,829 | 6/1991 | Edwards et al. | 137/859 X |
| 5,215,538 | 6/1993 | Larkin | 137/859 |

FOREIGN PATENT DOCUMENTS

| | | |
|---|---|---|
| 0072800B1 | 3/1983 | European Pat. Off. . |
| 4039814A1 | 6/1992 | Germany . |
| 2027168 | 2/1980 | United Kingdom . |

*Primary Examiner*—Gerald A. Michalsky
*Attorney, Agent, or Firm*—Baker & McKenzie

[57] ABSTRACT

A nonreturn valve for use in controlling the flow of medical fluid. The valve has two mating valve shells which carry and communicate with first and second pipe connectors, respectively. A diaphragm with a protrusion on its periphery is held between the valve shells. Circumferentially disposed retaining formations on each of the valve shells causes pretension to occur in the diaphragm upon assembly of the valve shells. The axial location of the retaining formation on the valve shell which carries the valve seat is such that tension in the diaphragm lightly urges the diaphragm into sealing engagement with the valve seat, whereby a seal exists when there is no significant pressure on either side of the diaphragm.

6 Claims, 1 Drawing Sheet

NONRETURN VALVE FOR MEDICAL FLUID TECHNOLOGIES

BACKGROUND AND SUMMARY OF THE INVENTION

The present invention relates to a nonreturn or check valve for use in medical fluid applications.

It is the state of the art (for example, as shown in DE 40 39 814 A1 and U.S. Pat. No. 4,966,199) to design a nonreturn valve with a two piece housing providing a first pipe connector and a second pipe connector between which a diaphragm made of a flexible material is located. Upon overpressure in the first or second pipe connector, the diaphragm is lifted from its sealing seat and a flow passage is created. Respective overpressure on the side opposite the sealing seat forces the diaphragm quickly and safely against the sealing seat, thus shutting the flow passage.

The solution shown in DE 40 39 814 A1 aims at improving the nonreturn valve through increased independence from manufacturing tolerances, and at achieving safe opening and shutting at lowest pressure differences. The design features a diaphragm with a circumferential section clamped into the housing, a central sealing section, and a thinner annular wall connecting both sections. Sealing effects, as well as opening times, depend on the way the diaphragm is clamped, which cannot be done reliably when the manufacturing tolerances are too high. The diaphragm can be subjected to an external, radial load to increase the opening force, but this does not help to improve the operational characteristics. In the known design, a high pretension can only be achieved by providing the diaphragm with a specifically designed thinner annular wall. In the known solution, the pretension is in a section of the diaphragm with reduced wall thickness; the absolute pretension may therefore not be very high.

The second solution shown in U.S. Pat. No. 4,966,199 features a loose, unperforated diaphragm, i.e. the circumference of the diaphragm is not clamped, and central and border sections move axially according to the operating conditions. Special elements are therefore provided to support the diaphragm in a centered position. Opposite flow directs the reflux toward the center of the downstream surface of the diaphragm. The reflux lifts the diaphragm from the supporting edges, over which it is bent during forward flow, and seals it off against a concave sealing surface. A flow converter protects this diaphragm against high pressure during forward flow, and the concave sealing surface protects it against high reflux pressure. Upon absence of forward or backward fluid pressure, the diaphragm assumes a neutral position where it forms a line contact with a curved, convex surface on the upstream side of the diaphragm, thus shutting off any reflux.

Such nonreturn valves are used in medical engineering for ducts in infusion systems, diagnosis equipment, syringes, intravenous tubes, etc. The following requirements must be met my such nonreturn valves:

a) the nonreturn valves must shut off very safely within fractions of a second to avoid any reflux of fluids contaminated with undesired agents; and b) their protection must be not only economical but with a high statistical safety.

There are strict laws requiring thorough examinations to ensure a consistent and long-lasting operational safety. The operational safety of such nonreturn valves is checked by the German Technical Surveyance Institution (Technischer Uberwachungsverein TUV), for example, permitting the medical application of such nonreturn valves only after thorough examination.

The invention provides a solution to the problem of creating a quickly and safely shutting nonreturn valve by exerting a radial tensile stress on the diaphragm.

The advantages achieved through this invention are in particular the quicker and equally safe operation of the nonreturn valve permitted by suitable adjustment of the tensile strength. Furthermore, reaction time and opening pressure can be influenced by adjusting the tensile stress through geometry modification. The production of the individual parts is extremely cost-efficient and statistically safe. For transmitting the increased pretension, the diaphragm border has a bulge which is simple to produce by injection molding, and favorably the wall thickness of the diaphragm center is not reduced. These two features are of advantage for the safe clamping, and the transmission of high tensile forces, respectively.

A favorable design example of the invention features the two valve shells with an inner and an outer annular protrusion, respectively, which are intermeshing for joining both valve shells together. The advantage of this is the generation of a clamping force exerted onto the bulge of the diaphragm.

The radial transmission of clamping and tensile forces is furthermore supported by the fact that the bulge and the corresponding walls of both valve shells are provided with approximately identical annular, slanting surfaces. When the parts are dislocated, the force is transmitted without play to the bulge of the diaphragm.

For production technology and operational reasons, it is of advantage to design the bulge with radii as cross-sectional boundary.

Further advantages are achieved by equipping the first valve shell with an annual sealing lip, and the second valve shell with several stroke limiting nubs equally spaced on a pitch circle axially opposite the sealing lip. The sealing lip is located more centrally toward the openings of the diaphragm.

Production and operational safety of the parts to be assembled are further improved by the fact that both valve shell walls forming the outer, radial border of the cavity have an annular protrusion of semicircular cross-section.

The radial tensile strength is further supported by the fact that the sealing lip protrudes further from the valve shell wall than the annular, semicircular protrusion.

A design example of the invention is presented in the drawing and described in detail below.

The objects and advantages of the invention will be better understood upon a reading of the following specification read in conjunction with the accompanying drawings.

DETAILED DESCRIPTION OF THE INVENTION

Figure 1:
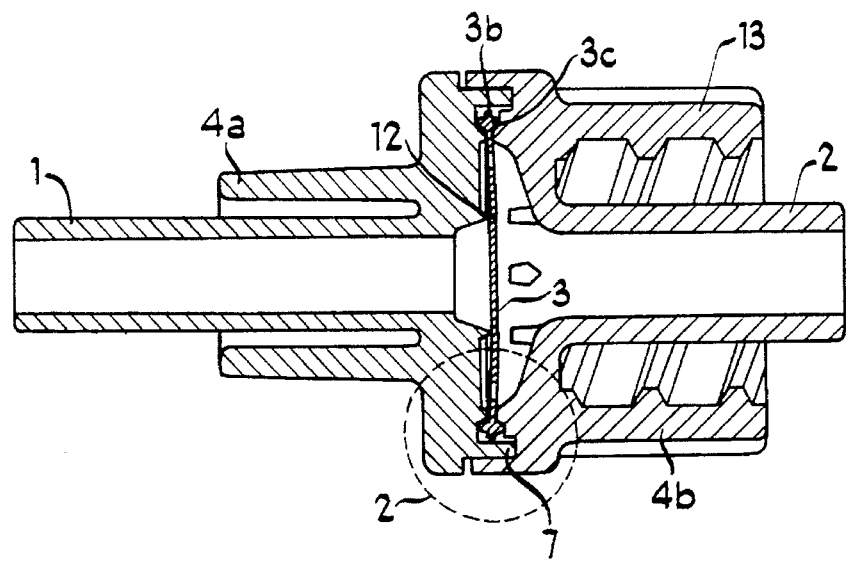
FIG. 1 is an axial cross-section of an assembled nonreturn valve according to the invention.

The design of the nonreturn valve is tailored to the specific requirements of medical engineering fluid technology applications. It is particularly suitable for pressure differences in the range of 0.1 to 0.002 bar. It consists basically of a first pipe connector 1 and a second pipe connectors 1 and 2. A diaphragm 3 made of a flexible material, e.g. silicone, is clamped between both pipe connectors 1 and 2. The central section of diaphragm 3 has a mainly consistent wall thickness permitting the transmission of considerable tensile forces in radial direction inward and outward. The outer circumferential section of diaphragm 3 has a bulge formed by injection molding, which is annularly arranged on the entire circumference or at least on parts of the circumference. After their assembly, the first valve shell 4a of the first pipe connector 1 and the second valve shell 4b of the second pipe connector 2 form a cavity 5. A wall surface 6 pointing radially outward is adjacent to bulge 3c such that upon assembly of both valve shells 4a and 4b, tensile forces are transmitted with radial orientation in the diaphragm 3.

Figure 2:
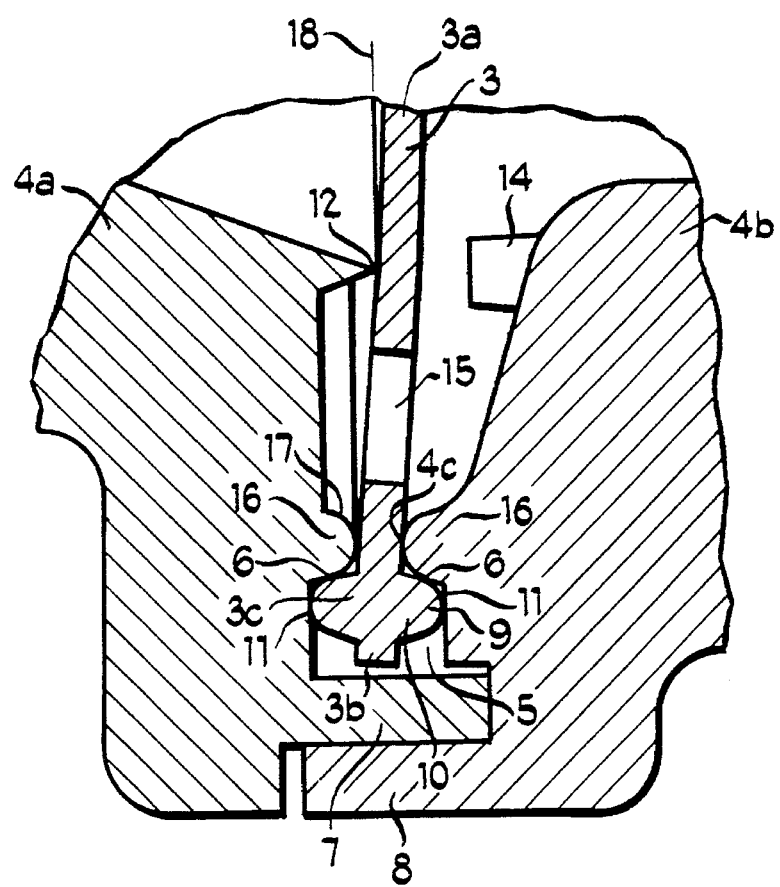
FIG. 2 is an enlarged sectional view of area "X" from FIG. 1.

Both valve shells 4a and 4b can be joined via an inner annular protrusion or rim 7 of the first pipe connector 1 and an outer annular protrusion 8 of the second pipe connector 2, which are close fitting and interlocking. The valve shells can be joined by ultrasonic welding, for example. Bulge 3c and the corresponding wall surface 6 (of which only one is necessary) in valve shells 4a and 4b have slanting surfaces, which are approximately identical. The boundary of cross-section 10 of bulge 3c is formed by radii 11. In the first valve shell 4a of the first pipe connector 1, an annular sealing lip 12 is formed. The second valve shell 4b, which is designed as a Luer-Lock connector 13, has several stroke limiting nubs 14 evenly distributed on the circumference, such that they are located axially opposite the sealing lip 12. The face of sealing lip 12 is located inside the inner edges of the openings 15, which extend through the outer portions of the diaphragm 3. The wall surfaces 6 of cavity 5 have a semi-circular cross-section 16 pointing radially outward and form an annular protrusion 17 to the corresponding valve shell 4a or 4b. With respect to the radial plane 18, the annular protrusion 17 does not protrude from the inside of the shell 4a as far (to the right of FIGS. 1 and 2) as the opposing sealing lip 12. The sealing lip 12 is formed by two intersecting frustoconical surfaces which converge to form as sharp an edge as possible. The included angle of the surfaces forming the sealing lip 12 is about 40°.

While a specific embodiment of the invention has been shown and described, it will be apparent to those skilled in the art that numerous alternatives, modifications, and variations of the embodiment shown can be made without departing from the spirit and scope of the appended claims.

I claim:

1. A nonreturn valve, particularly for medical fluid technology applications, comprising a first pipe connector defining an inlet and having a sealing seat, and a second pipe connector defining an outlet, and a diaphragm made of a flexible material, which is located between said pipe connectors and which can be lifted from said sealing seat upon overpressure in said inlet, thus creating a flow opening, said diaphragm capable of being pressed against said sealing seat upon overpressure in said outlet, the diaphragm having a central section and an outer section with a bulge on its periphery, a first valve shell of the first pipe connector and a second valve shell of the second pipe connector forming a cavity housing the bulge but leaving an opening for said diaphragm, one wall surface of the cavity pointing radially outwardly and being adjacent to said bulge such that tensile forces are created in the diaphragm upon assembly of both valve shells, each of said valve shells having an inner and an outer annular protrusion, said outer protrusions fitting closely within each other and providing means for said valve to be assembled, at least one of said valve shells having a slanted wall surface on its inner annular protrusion which abuts an opposing inwardly facing surface of said bulge, said slanted surface of said valve shell being circumferentially continuous and slanting at a slope which is approximately the same as the slope of said inwardly facing surface of said bulge, said bulge having rounded surfaces defining a generally ovoid cross-section, the first valve shell of the first pipe connector having an annular sealing lip, and the second valve shell having several stroke limiting nubs opposite the sealing lip, with the sealing lip located inside inner edges of openings in the diaphragm, said inner annular protrusions being rounded in cross-section, one of said valve shells having a base which carries said lip and a first one of said inner annular protrusions, said first inner protrusion extending from said base an axial extent which is less than the extent to which said lip extends from said base.

2. A nonreturn valve according to claim 1 wherein:
   said tensile forces and assembly of said valve shells cause said diaphragm to be urged against said sealing lip.

3. A nonreturn valve according to claim 2 wherein:
   said sealing lip has a sharp edge formed by two intersecting frustoconical surfaces, said surfaces defining an included angle of about 40°, whereby the pressure exerted by said lip upon said diaphragm is increased.

4. A nonreturn valve for medical and fluid technology applications comprising a first pipe connector and a second pipe connector between which a membrane disc made of a flexible material is held lifted from a sealing seat upon overpressure in the inlet, and which requires minimum time for being pressed safely against the sealing seat upon overpressure in the outlet, the central part of the membrane disc being predominantly uniform in thickness, the outer circumferential section of the membrane disc having an annular bulge, a first shell of the first pipe connector and second shell of the second pipe connector forming a hollow space which surrounds the bulge except for a gap of approximately the same size as the thickness of the central part of the membrane disc, at least one surface of the hollow space facing outwardly pressing against the protrusion in such a way that, upon assembly of both shells, radially oriented tensile forces can be induced in the membrane disc, said at least one surface having a slope, the bulge having a rounded cross-sectional profile, and the radially outward facing surface forming part of an annual recess on the associated shell, the first shell of the first pipe connector having an annular sealing lip, the second shell having a plurality of stroke limiting knobs distributed within said second shell located opposite the sealing lip, said membrane disc having openings therethrough, and the sealing lip having a radial extent such that said lip engages said membrane disc at locations which are disposed radially inwardly of said openings.

5. A nonreturn valve according to claim 4 characterized by the feature that the sealing lip protrudes in a radial plane with respect to the annular protrusion.

6. A nonreturn valve according to claim 4 wherein:
   said shells are connected to each other by an inner annular rim formed on one of said shells, and an outer annular rim formed on the other of said shells, with said annular rims having close-fitting dimensions.

\* \* \* \* \*